US00PP12345P2

(12) United States Plant Patent

Sharma

(10) Patent No.: US PP12,345 P2

(45) Date of Patent: Jan. 8, 2002

(54) NEW GUINEA IMPATIENS PLANT NAMED 'OVATION HOT LAVA'

(75) Inventor: Jagan N. Sharma, Nipomo, CA (US)

(73) Assignee: Waller Genetics, Inc., Guadalupe, CA (US)

( * ) Notice: Subject to any disclaimer, the term of this patent is extended or adjusted under 35 U.S.C. 154(b) by 0 days.

(21) Appl. No.: 09/550,516

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Hot Lava, characterized by its red-orange flower color, deep green leaves, early flowering, long-lasting flowering, self-branching and vigorous habit.

1 Drawing Sheet

The present invention relates to a new and distinctive cultivar of Impatiens plant, botanically known as *Impatiens Hawkeri*, commercially known as New Guinea Impatiens, and known by the cultivar name 'Ovation Hot Lava'. Ovation Hot Lava was developed in a controlled breeding program by crossing Waller Seedling No. 96-1J-77-1 (seed parent) with Waller Seedling No. 93-1J-50 (pollen parent). Both parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Hot Lava has Orange-Red Group 40A colored flowers while Harmony Orange (unpatented) and Celebration Orange (U.S. Plant Pat. No. 10,078) both have Orange-Red Group 33A colored flowers.
2. Ovation Hot Lava has a small light lavender pink eye in the center of the flower while Harmony Orange and Celebration Orange have a carmine eye.
3. Ovation Hot Lava is intermediate in flower size at 7.0 to 7.5 cm in diameter with Harmony Orange having smaller flowers at 6.0 to 6.5 cm and Celebration Orange having larger flowers at 7.5 to 8.0 cm.
4. Ovation Hot Lava is similar in height to Harmony Orange but more compact than Celebration Orange.
5. Ovation Hot Lava has deep green leaves while Harmony Orange has dark green with red-purple cast leaves and Celebration Orange has medium green leaves.
6. Ovation Hot Lava has leaves that are 10 to 11 cm long which is similar to Harmony Orange but smaller than Celebration Orange which has 13 to 14 cm long leaves.
7. Ovation Hot Lava has red-purple pedicels while Harmony Orange has a yellow-green pedicel and Celebration Orange has a yellow-green with slight red-purple cast pedicel.
8. Ovation Hot Lava has a red-orange cast to the anther hood while both Harmony Orange and Celebration Orange each have an anther hood with a red-purple cast.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorus with nutritional trace elements added. Habit of growth, foliage coloration, leaf variegation, size of leaves, and flower size will be greatly influenced by nutritional and environmental conditions.

Color references are made to The Royal Horticultural Society Colour Chart except where general terms of ordinary dictionary significance are used.

Parentage: A controlled cross between female parent Waller Seedling No. 96-1J-77-1 and male parent Waller Seedling No. 93-1J-50.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fiborous.

Plant description:

(*A*) *Form and habit of growth.*—Mounded to semi-upright, self-branching, intermediate in height, flowers open over the top of leaf canopy; continuous flowering; vigorous growing flowering herb. Average height is 21 to 25 cm and average width is 45 to 50 cm. Internode length is 5 to 6 cm but is highly variable. Pedicel is Greyed-Purple Group 184B, stem is Greyed-Purple Group 185A, and internode is Greyed-Purple Group 185A. Pedicel length is 4 cm.

(*B*) *Foliage description.*—Deep green with light green midrib and no leaf variegation. (1) Size: 10 to 11 cm long and 3.0 to 3.5 cm wide on average mature leaf.

(2) Shape: Lanceolate with acuminate apex and acute base. (3) Texture: Both upper and lower surfaces are glabrous. (4) Margin: Finely serrated with fine cilia. (5) Color: Young foliage, top side is Yellow-Green Group 147A, underside is Yellow-Green Group 147B; Mature foliage, top side is Yellow-Green Group 147A, underside is Yellow-Green Group 147B. (6) Venation: Pinnate, upper side is Yellow-Green Group 147B and lower side is Greyed Purple Group 184D. (7) Young midrib is Greyed-Purple Group 184C and mature midrib is also Greyed-Purple Group 184C.

(*C*) *Branching.*—The branching is naturally occurring. Lateral branching at base: 5 or more lateral branches. Lateral branch length is 15 to 18 cm but is highly variable.

Flowering description:

(*A*) *Flowering habits.*—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season.*—Indeterminant and continuous; quantity of flowering increases with increasing levels of light.

(*C*) *Flower bud description.*—Ellipsoidal; flowers perfect; spur is 5.0 cm long on mature bud, with the throat behind the ovary and originating from the major sepal. Bud length is 18 to 20 mm and bud diameter is 14 mm. Spur is Red-Purple Group 60A, spur tip is Red-Purple Group 59A, flower bud is Red Group 42A just before opening, and eye is Red-Purple Group 60C.

(*D*) *Flowers borne.*—On individual red-purple pedicels 4.0 cm long from a whorl of usually five leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—7.0 to 7.5 cm. Flower Depth: 5 mm.

(*G*) *Petals.*—(1) Shape: Heart, standard is largest petal. (2) Color: Top side in winter when opening is Red Group 40A with small eye at center of Red Group 54D, no fading; underside is Red Group 41B. (3) Number of petals: Five. (4) Size of petals: Standard: 5.0 cm wide and 3.0 cm long, two equal lobes with moderate cut. Wings: 3.5 cm wide and 3.0 cm long, two unequal lobes with moderate cut. Keel: 4.0 cm wide and 3.5 cm long, two unequal lobes with moderate cut.

(*H*) *Reproductive organs.*—(1) Stamens: Five in number. (a) Anther: Hooded shape, color is Yellow-White Group 158C with a Red Group 44B cast. (b) Pollen color: Yellow-White Group 158C. (2) Pistils: (a) Stigma: Five, segmented column, color is White Group 155B. (b) Style color: White. (c) Ovaries: Five in number, size is 7 mm when immature, color is Yellow-Green Group 146A.

Disease resistance: No significant disease or insect problems seen to date.

(*I*) *Fertility.*—The plants are fertile, but do not normally set seed under greenhouse or garden conditions, unless in a controlled crossing program.

OTHER IMPORTANT CHARACTERISTICS

1. Self-branching early flowering nature allows cultivar to be grown in 10 cm pots but is also vigorous enough to be grown in 15 to 25 cm containers as well.

2. Minimal fading of older flowers, large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Hot Lava, as illustrated and described.

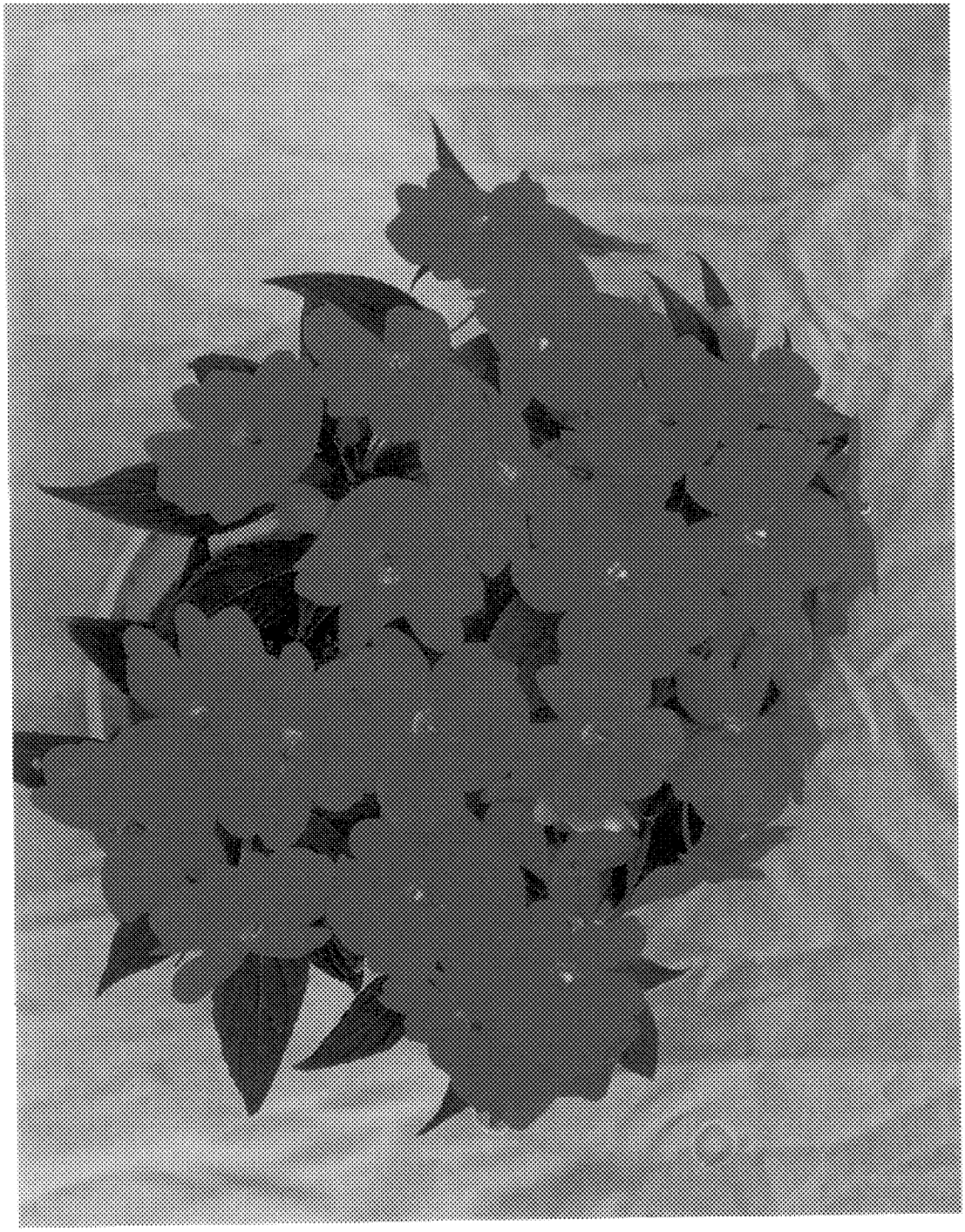

* * * * *